Figure 1:
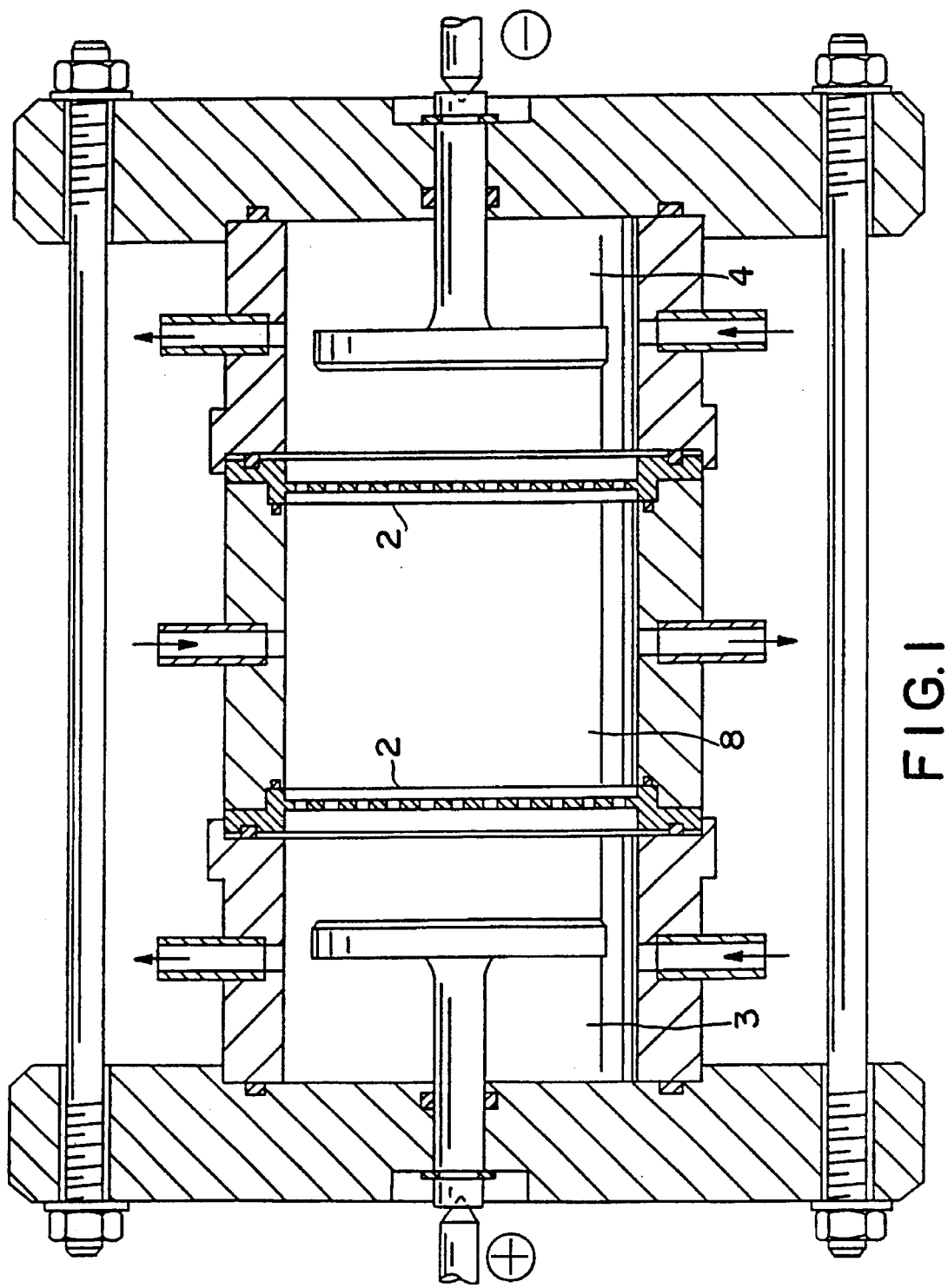

United States Patent [19]

Linder et al.

[11] Patent Number: 5,599,506

[45] Date of Patent: Feb. 4, 1997

[54] IMMOBILIZED BUFFERED GELS AND MEMBRANES OF HYDROXY GROUPS CONTAINING POLYMERS

[75] Inventors: Charles Linder, Rehovot; Mara Nemas, Neve Monoson; Mordechai Perry, Petach Tikva; Reuven Ketraro, Rishon Letzion, all of Israel

[73] Assignee: Aligena AG, Basle, Switzerland

[21] Appl. No.: 417,113

[22] Filed: Apr. 5, 1995

Related U.S. Application Data

[62] Division of Ser. No. 67,617, May 27, 1993, Pat. No. 5,430,099.

[30] Foreign Application Priority Data

May 28, 1992 [GB] United Kingdom .................. 9211324

[51] Int. Cl.$^6$ ............................................. C08F 8/00
[52] U.S. Cl. ......................... 422/131; 422/135; 525/61; 536/31
[58] Field of Search .................................. 422/131, 135, 422/224; 536/31; 525/61, 328.8, 351, 379, 382; 204/299 R, 302, 307; 366/152, 160, 177

[56] References Cited

U.S. PATENT DOCUMENTS

| | | | |
|---|---|---|---|
| 3,539,661 | 11/1970 | Rauch-Puntigam | 260/856 |
| 3,914,168 | 10/1975 | Allington | 204/299 |
| 3,915,839 | 10/1975 | Rilbe et al. | 204/299 |
| 4,016,149 | 4/1977 | Travis et al. | 260/122 |
| 4,229,537 | 10/1980 | Hodgins et al. | 435/177 |
| 4,245,064 | 1/1981 | Drobnik et al. | 525/329 |
| 4,319,975 | 3/1982 | Cook | 204/180 G |
| 4,506,987 | 3/1985 | Daughton et al. | 366/160 |
| 4,562,251 | 12/1985 | Fulton et al. | 536/17.4 |
| 4,971,671 | 11/1990 | Faupel et al. | 204/182.8 |

FOREIGN PATENT DOCUMENTS

| | | |
|---|---|---|
| 0050389 | 4/1982 | European Pat. Off. . |
| 0184361 | 6/1986 | European Pat. Off. . |
| 0287513 | 10/1988 | European Pat. Off. . |
| 0323948 | 7/1989 | European Pat. Off. . |
| 0369945 | 5/1990 | European Pat. Off. . |
| 2243438 | 4/1975 | France . |
| 2287912 | 5/1976 | France . |
| 2418245 | 9/1979 | France . |
| 870438 | 6/1961 | United Kingdom . |
| 880624 | 10/1961 | United Kingdom . |
| 1041523 | 9/1966 | United Kingdom . |
| 1381380 | 1/1975 | United Kingdom . |
| 1461528 | 1/1977 | United Kingdom . |
| 1540165 | 2/1979 | United Kingdom . |
| WO79/00609 | 8/1979 | WIPO . |

OTHER PUBLICATIONS

Derwent Abstract AN 91–028156, "Extraction of Luciferase From Luciola Mingrelica", 1990.
Wenger et al., Journal of Biochemical and Biophysical Methods, 14, 29–43 (1987).
Migliaresi et al., Journal of Biomedical Materials Research, 15, 307–317 (1981).

Primary Examiner—Christopher Kim
Attorney, Agent, or Firm—Wenderoth, Lind & Ponack

[57] ABSTRACT

A gradient mixer for the preparation of immobilized pH-gradient (IPG) gels, which includes a positive displacement syringe dispensing device (4,5) driven by a controlled speed motor (1); a mixer driven by a magnetic stirrer (6); a temperature controlled circulating air oven for the mixer/dispensing syringes (7); a cassette into which mixed solutions of acidic/basic gels are dispensed and the IPG gel is shaped (9); and a second temperature controlled circulating air oven for the cassette (8).

1 Claim, 2 Drawing Sheets

IMMOBILIZED BUFFERED GELS AND MEMBRANES OF HYDROXY GROUPS CONTAINING POLYMERS

This is a divisional application of Ser. No. 08/067,617, filed May 27, 1993, now U.S. Pat. No. 5,430,099

The present invention relates to immobilized buffered gels and their use in electrophoretic processes, particularly in preparative isoelectric focusing (PIEF) for separating (high molecular) organic compounds, such as proteins or peptides from biological mixtures, and in immobilized pH-gradients for isoelectric focusing slabs and columns.

More particularly, the present invention is directed to new polymeric reaction products and methods for their preparation, and their use for preparing said immobilized buffered gels of for example a fixed pH-value or of a pH-gradient. These gels are suitable media for preparing membranes, plates or columns, such as plates or columns of immobilized pH-gradient gels (IPG-gels) which can be used e.g. in capillary electrophoresis (CE).

Biologically active materials require high purity to prevent deleterious side effects by impurities, which are often also biologically active. This is especially true, and particularly difficult to achieve, for proteins made by biotechnological processes, such as fermentations, because they may contain other proteins (as impurities) separated by each other by as little as 0.001 pI units (pI=isoelectric point).

(Preparative) isoelectric focusing is one of the few practical (electrophoretic) methods for achieving protein purification for such closely matched molecules. It is certainly the most economical method when it can be made to work.

A continuously working PIEF-device is for example disclosed in EP-A-287 513, using polyacrylamide gel membranes. These membranes are, however, toxic because of their carcinogenic monomer (acrylamide), and attempts for making nontoxic gel(membranes) from, for example, agarose were not highly successful (P. Wenger et al., J. of Biochemical and Biophysical Methods 14, 29–43 (1987)). The polyacrylamide gels are also relative weak mechanically.

Polyacrylamide gels are further limited in PIEF-processes by a considerable sieving effect which does not allow free flow of protein molecules with molecular weights greater than 500 kDa (kilo-Dalton). This prevents the efficient separation of high molecular weight proteins or viruses in the preparative or analytical devices (gel membranes, IPG-plates or columns).

Derivatized agarose and its utilisation for gel electrophoresis are disclosed in U.S. Pat. No. 4,319,975 to Cook. The agarose derivatives, among them those of non-ionic triazines, show a decrease in pore size which is useful for sieving properties. These derivatives are useful for continually moving molecules, but are not applicable to isoelectric focusing. Further, the Cook reference does not teach the production or the application of immobilized buffering groups on polymers and their formation into PIEF or IPG gels.

While the polyacrylamide gels are not entirely satisfactory as PIEF gels and the non-ionic agarose derivatives cannot be used as such, these disadvantages can be overcome by the inventive gels which are non-sieving gels for free passage of all molecules and contain acid and basic groups together in the right proportions to give buffering capacity, at a fixed pH-value. Other advantages of the inventive gels are their low toxicity and better pH-stability.

Therefore, it is one object of the present invention to provide new reaction products of a hydroxy group containing neutral polymer with an anionic (acidic) or cationic (basic) diazine or triazine derivative.

Other objects of the present invention are the process of the preparation of said reaction products, an immobilized buffered gel which comprises an optionally cross-linked matrix of a mixture of said acid and basic reaction products, a process for the preparation of the immobilized buffered gels, the formation of the gels into membranes or immobilized pH-gradient gel plates or columns, the gradient mixer to prepare these membranes, plates and columns, as well as their use in preparative isoelectric focusing electrophoresis, e.g. for separating biologically active components from biological mixtures.

These and other objects of the present invention will become apparent from the following detailed description.

The inventive reaction products are preferably those wherein the hydroxy group containing neutral polymer is a natural or a synthetic homo- or copolymer and the diazine or triazine derivative is a reactive acid reaction product of (a) an amino-carboxylic or amino-sulfonic acid and (b) a di- or triazine containing a nucleophlic leaving group, or a reactive basic reaction product of (c) a mono- or polyamine and (b) a di- or triazine containing a nucleophilic leaving group.

Suitable, natural hydroxy group containing polymers are e.g. the polysaccharides, preferably agarose.

The synthetic homo- or copolymers can be selected from the vast number of hydroxy group containing polymeric species; preferred are the polyvinyl alcohols or the copolymers on the basis of vinylalcohol; further a poly-(hydroxyalkyl)- or a poly-(hydroxyalkoxyalkyl)-acrylate or-methacrylate, a homopolymer based on an N-acryloyl(methacryloyl)-tris-(hydroxyalkyl)aminomethane, or a copolymer of a hydroxyalkylacrylate or -methacrylate or a hydroxyalkoxyalkyl acrylate or -methacrylate and at least one comonomer, or a block co- or terpolymer of said (meth)acrylates and at least one of said comonomer.

In these compounds alkyl and alkoxy each independently represent lower alkyl or alkoxy radicals with e.g. 1 to 5, preferably 1 to 3 carbon atoms, such as methyl, ethyl, propyl, methoxy, ethoxy or propoxy.

Suitable copolymers on the basis of vinylalcohol are those containing as comonomers e.g. ethylene, methyl(meth)acrylate, N-vinylpyrrolidone, or preferably a hydroxyalkyl acrylate or methacrylate with alkyl of 1 to 3 carbon atoms.

Suitable comonomers that can be copolymerized with the hydroxyalkyl/hydroxyalkoxyalkyl-acrylates or methacrylates are e.g. vinyl ethers, such as vinylethylether; vinyl esters, such as vinyl acetate; N-vinyl pyrrolidone; a mono- or poly-(alkoxy)-alkyl acrylate or methacrylate, such as methoxyethyl methacrylate, methoxyethoxyethyl methacrylate, or methoxydiethoxyethyl methacrylate, or an alkylene ($C_2$–$C_4$)glycol di-acrylate or-methacrylate.

Suitable and preferred homopolymers are those based on hydroxyethyl methacrylate, hydroxyethoxyethyl methacrylate or hydroxydiethoxyethyl methacrylate, or a homopolymer based on N-acryloyl-tris-(hydroxymethyl)-aminomethane(NAT).

The reactive acid reaction product (which will be reacted with the polymer) of (a) an amino-carboxylic or amino-sulfonic acid and (b) a di- or triazine containing a nucleophilic leaving group comprises as (a) an alkylamino carboxylic or alkylamino sulfonic acid, each independently containing alkyl of preferably 1 to 6 carbon atoms. Examples are: amino glycolic acid, glycine, 3-amino propanoic acid, 4-amino butyric acid, or 2-amino propane sulfonic acid.

The di- and triazines (b) contain at least two nucleophilic leaving groups (groups that are split off when the component undergoes a nucleophilic substitution reaction) which are first of all halogen atoms, such as bromo, but preferably fluoro and chloro; further ammonium, such as tri(lower-)alkyl ammonium or (optionally substituted) pyridinium; sulfo or sulfonium ($R_3S^+$-, $R=C_1-C_4$-alkyl); and phosphonium.

Representative examples of the di- and triazines are:

(A) s-triazines containing at least two reactive identical or different halogen atoms bound to carbon atoms, for example cyanuric chloride, cyanuric fluoride, cyanuric bromide and also primary condensation products of these cyanuric halides and, for example, water, ammonia, amines, alkanols, alkylmercaptans, phenols or thiophenols; further phenols, anilines, alkanols and alkylamines containing ionic groups which will render the dihalogenated triazines water-soluble. Such ionic groups are sulfonic, carboxylic, quaternary ammonium, sulfonium or phosphonium groups;

(B) pyrimidines containing at least two reactive identical or different halogen atoms, such as 2,4,5-trichloro/trifluoro/tribromo-pyrimidines, which can be further substituted in 6-position, for example by alkyl, alkenyl, phenyl, carboxyl, cyano, nitro, chloromethyl, chlorovinyl, carbalkoxy, carboxymethyl, alkylsulfonyl, carboxamido or sulfamido, but freferably by halogen (fluoro, chloro, bromo). Particularly suitable halogeno pyrimidines are 2,4,5-trichloro-, 2,4-difluoro-5-chloro- or 2,4,5,6-tetrachloro-pyrimidine; further water-soluble derivatives of pyrimidine similar to those of (A), above, which do not contain acid or basic groups, which are not replaceable and which contribute to the pH.

(C) halogenopyrimidine-carboxylic acid halides, for example dichloropyrimidine-5- or -6-carboxylic acid chloride;

(D) 2,3-dihalogeno-quinoxaline- or-phthalazine-carboxylic acid halides or-sulfonic acid halides, such as 2,3-dichloroquinoxaline-6-carboxylic acid chloride or bromide;

(E) halogeno-6-pyridazonyl-1-alkanoyl halides or-benzoyl halides, for example 4,5-dichloro-6-pyridazonl-1-propionyl chloride or-1-benzoyl chloride.

The preferred compounds are s-triazines and pyrimidines substituted by active leaving groups, such as halogen atoms, prefearably fluoro and chloro, quternary ammonium groups or sulfo (—$SO_3H$).

The reactive basic reaction product (which will be reacted with the polymer) of (c) a mono- or polyamine and (b) a di- or triazine containing a nucleophilic leaving group comprises as (c) an alkylmono- or an alkylene polyamine of 4 to 10 carbon atoms. Representative examples of (c) are 2-aminoethyl-morpholine, 3-aminopropyl-morpholine, 2-(dimethylamino)-ethylamine, 3-(dimethylamino)-propylamine, 3-(diethylamino)-propylamine, and 2-(triethylammonium)-ethylamine chloride. Component (b) is as defined above.

Examples of the reactive acid reaction products (which impart buffer capacity to the polymers (gels)) are: 1-(amino-2-propane sulfonic acid)-3,5-dichlorotriazine, 1-(amino glycolic acid)-3,5-dichlorotriazine, 1-(glycino)-3,5-dichlorotriazine, 1-(amino propanoic acid)-3,5-dichlorotriazine, 1-(amino-butyric acid)-3,5-dichlorotriazine. Examples of the reactive basic reaction products which also are used to impart buffer capacity to the the polymers are: 1-(2-morpholino-ethylamino)-3,5-dichlorotriazine, 1-(3-morpholino-propylamino)-3,5-dichlorotriazine, 1-(2-dimethylamino-ethylamino)-3,5-dichlorotriazine, 1-(3-dimethylamino-propylamino )-3,5-dichlorotriazine, 1-(3-diethylamino-propylamino )-3,5-dichlorotriazine and 1-(2-triethylammonium-ethylamino)-3,5-dichlorotriazine chloride.

The reactive acid and basic reaction products can be prepared by reacting (a) or (c) with (b) according to known chemical processes. The acid or basic moiety does not react with (b) under the conditions employed. The acid groups are preferably chosen from carboxylic acids, and the amino groups are chosen from tertiary alkyl or heterocyclic amines. These amines should not react under the conditions of use with the other reactive groups of (b) (or of different reagents which may be used to cross-link the polymer (gel)), and this generally means that the alkyl side chain should contain more than one carbon atom in at least two of the alkyl radicals (which prevents reactivity of tertiary amines with halo triazines or diazines because of steric hindrance, and the heterocyclic amines should contain sterically arranged groups which prevent reactions).

Where the heterocyclic amines can react with component (b) to form quaternary ammoniums, they should react much slower than the designed binding groups, and if they react at other conditions after the acid/basic reaction products (buffering reagents) are bound, they should form reactive groups which can be displaced by the functional group of the polymer (gel) to bind the buffering reagents to the polymers (gels).

The acid and basic diazine and triazine derivatives as hereinbefore described (which serve as pH-determining moieties) are reacted with a hydroxy group containing neutral polymer; the resulting acid and basic polymeric reaction products are mixed together (titrated against each other) to form a solution of the desired pH-value, set in a mold and then gelled, e.g. by lowering the temperature (when agarose derivatives are used) or by chemically cross-linking. These immobilized buffered gels constitute a further object of the present invention.

The inventive gels can be prepared by various processes, one of which comprises reacting simultaneously the acid and the basic diazine or triazine derivatives with the hydroxy group containing neutral polymer in a mold and gelling them.

Alternate routes to the inventive immobilized buffered gels comprise (1) reacting separately the acid diazine or triazine derivative and the basic diazine or triazine derivative each with the hydroxy group containing neutral polymer, (2) titrating the polymeric reaction products of (1) batchwise against each other to form a polymeric mixture of a predetermined single pH-value, or in a continuous manner to form a polymeric mixture of a pH-gradient, and (3) casting the polymeric mixtures of (2) into a mold and gelling them; or (1) reacting a reactive diazine or triazine, non-derivatized with an acid or basic pH-determining compound, with the hydroxy group containing neutral polymer, (2) reacting the polymeric reaction product of (1) separately with an acid and an basic pH-determining compound, (3) titrating the polymeric reaction products of (2) batchwise against each other to form a polymeric mixture of a predetermined single pH-value, or in a continuous manner to form a polymeric mixture of a pH-gradient, and (4) casting the polymeric mixtures of (3) into a mold and gelling them.

The preparation of the derivatized polymers (gels) may thus take different pathways: In one approach, the triazine or diazine derivatives of the acid or basic buffer (compound with a pH-determining moiety) are prepared and then reacted with the polymer. In this case, the reactive reagent may be prepared in preferably non-aqueous solutions or in aqueous ones when one of the components is not soluble. The derivative is then reacted with the gel at a pH and temperature which is allowed by the second halogen atom on the triazine and which leaves the third halogen atom unreacted. In the case of triazines, the cyanuric chloride is derivatized with the acid or basic buffering groups at 0° to 10° C., and reacted with the gel at 15° to 25° C. Thus if, when working in aqueous solutions, the second chloro atom hydrolyzes to hydroxy, this derivative has only the third chloro atom, which is not reactive and will not react with the gel and will be washed out in the purification step.

Thus, after the derivatization of agarose or other polymers, the obtained polymeric products are purified. Being not cross-linked they are redissolved and titrated against each other to the proper pH-value and then formed into the desired configuration, and geller and/or crosslinked as required.

In an other approach the polymer may be first derivatized through its hydroxy groups with the underivatized halogeno di- or triazine (tetrachloro pyrimidine or preferably cyanuric chloride), the excess reagent washed away, and then reacted with the acid or basic compound. These compounds may be the said amino acids (e.g.4-aminobutyric acid) for the acid derivatives, and primary alkyl tertiary amines (e.g. 2-aminoethyl-morpholine) for the basic derivatives. They may also be, but less preferred, hydroxy acids or hydroxy tertiary amino derivatives. All the steps may be carried out in solution, but it is also advantageous to carry out the reactions on the polymer (gel).

It is further advantageous to work in non-aqueous systems whenever possible to avoid competitive hydrolysis of the active halogen atoms of the di- or triazines. Thus, for example, in the case of agarose, the gel is made from water solutions by lowering the temperature of the sol to get a gel, replacing the water with acetone, and reacting with cyanuric chloride in acetone with a non-nucleophilic acid acceptor, such as N,N-dimethyl aniline, diisopropyl amine or diisopropylethyl amine, at 0° to 5° C. After a period of time, the gel is washed off unreacted cyanuric chloride with acetone, then reacted with an excess of the acid or basic reagent to introduce the buffering groups, and the excess reagent washed out. This approach works well with the basic buffering reagents, as they dissolve well in non-aqueous solutions like acetone or tetrahydrofurane. The acid derivatives do not dissolve so well in non-aqueous solvents and must be used in general in aqueous mixtures or with bulky aliphatic or aromatic counter ions to the acid groups to increase solubility in solvents. An aqueous mixture that can be used is e.g. acetone/water (90/10).

Alternatively, the water of the gel can be replaced by a solvent like acetone, and the acetone swollen gel can be reacted with the triazine or diazine derivative in aprotic solvents, such as acetone, in order to bind the buffer groups to the gel. The gel is washed and then remelted and titrated to get the desired pH and buffer capacity.

In both, the polymerization to a gel and the cross-linking of an existing polymer, the relationship between such parameters as the degree of cross-linking, crystallinity, hydrophilicity and permeability are important. The gels (hydrogels) which do not innately form open network structures as e.g. agarose must be made into a sufficient porous structure, which is, nevertheless, mechanically strong.

A preferred way to form such a gel and a gel membrane would be as follows:

A solution of the (water-soluble) polymers are allowed to react, and a solvent swollen gel is formed when the polymer is cross-linked. Pore-forming agents (e.g. leachable polymers, cosolvents) may be used to get large pores. For example, the permeability of poly-(2-hydroxyethyl methacrylate) membranes (J. Biotaed. Mat. Res. 15, 307, 1981) have been studied, and it has been found that the structure of the membrane-forming gel depends on the amount of the cross-linking agent. At low concentrations of the cross-linking agent, the transport of water and solutes is possible through the pores present. At high concentrations of the cross-linking agent, the membranes are dense and block solute passage. In the case of polyvinyl alcohol (PVA), permeability is affected by the extent of crystallinity versus amorphous content, which can be controlled by choice of comonomers.

Other polymers, such as those based on NAT, form porous structures greater than polyacrylamides, even though they are formed in the same way of polymerization of the monomer and cross-linking during polymerization.

Agarose, a thermally reversible gel, on the other hand, forms gels with large pores on its own when cooled from a sol which are suitable for protein permeation.

In working with thermally reversible gels, such as agarose, the best way to form gel membranes is to first derivatize separately the agarose with the acid and basic di- or triazine derivative and then to isolate (for purification). The (polymeric) derivatives are then titrated against each other to the desired pH-range (single pH-point) for single pH membranes or continuously to form IPG at elevated temperature while in the sol state. To make a PIEF-membrane, the sol titrated to the required pH is cast in a mold and then left to cool and gel.

The reason for derivatizing the polymer prior to casting is that control over the pH or pH-gradient is is more accurately carried out by titration of preformed species in solution, than on gels already formed into the shaps they will be used.

For making IPG-gels in plate or column or capillary form, one agarose derivative in sol form is titrated continuously with one or more other agarose derivatives, and added to a mold while continuously titrating to get a continuous pH gradient. The sol is then left in the mold to gel and gives an IPG. In making the pH gradient, density gradients may be set up with gycerol or other suitable materials. Devices for continuous gradient making are well known in the state of the art. In working with sols and polymer solutions, it may not be necsessary to work with the said density gradient materials.

The inventive agarose derivatives are thermally reversible gels which are solid at room temperature and need no cross-linking. Other non-thermally reversible gel polymer derivatives (e.g. derivatized polyvinyl alcohol or poly-(hydroxyalkylmethacrylates)) must be cross-linked after they are formed in the desired configuration.

If the gel membrane is made from a thermally reversible gel, as would be the case with agarose, or from a water-swellable but not water-soluble polymer, then the gel does not have to be chemically cross-linked, although ist may be desirable to enhance extreme pH and chemical stability.

Room temperature soluble hydrophilic polymers, such as polyvinyl alcohol, should be cross-linked to prevent dissolution. The cross-linking may be done with a cross-linker which is the acid/basic di- and triazine derivative mentioned (buffering reagent—BR), when it contains two or more reactive (leaving) groups towards the functional groups (OH-groups) of the polymer (gel), with a cross-linker other than the BR, or with a combination of both.

In one preferred cross-linking mode, the BR does both the cross-linking and introduces the buffering moieties. The cross-linking should occur after the sol or polymer solutions have been titrated into the right pH range and formed as gels into the desired configuration (plates, columns or capillaries).

Preferred examples of BR are dichloro triazine derivatives of tertiary amines and alkyl carboxylic acids as mentioned hereinbefore.

Cross-linkers which only cross-link but do not buffer may be chosen from the list below (e.g. non-ionic triazine derivatives).

If non-thermally reversible polymers are used, then they are preferably derivatized first, purified and then mixed in the correct proportion by titration as required to achieve the correct pH or pH gradient, as described above for agarose. They are then placed in a mold, where they are subsequently cross-linked to maintain their shape and preserve the pH or pH gradient.

The cross-linking agents in this context are multi-functional reagents with groups that react with hydroxy groups and do not introduce ionic, acid or basic, groups. These include aldehydes, such as acetaldehyde or glutardialdehyde; diacids, such as maleic or oxalic acid; di-esters; di-isocyanates, such as $C_2$–$C_4$-alkylene di-isocyanates, e.g. ethylene di-isocyanate; epoxides (water-soluble); di-vinyl sulfones; free or etherified N-methylol ureas or N-methylol melamines, such as N,N-dimethylolurea, N,N-dimethylolurea dimethyl ether or trimethylolmelamine dimetyl ether; eerie redox systems; and most preferably diazines and triazines; of these latter ones tetrachloropyrimidine and in particular cyanuric chloride have proven especially advantageous.

In the approach to forming hydrogels from existing polymers, BR will be bound to the hydrophilic polymers prior to cross-linking to form the gel or be carded out during the cross-linking step. For example, BR with halogen di- or triazinyl groups may be prepared and then reacted with the pendants of the hydrogel polymers.

Good candidate polymers for this approach are hydrogels, such as agarose, polymers based on NAT and PVA. The BR may also be used with hydrogel monomers during polymerization to form cross-linked hydrogels. One benefit of this approach is improved pH stability over the ester or amide type BR. All BR achieve the maximum buffer capacity for the chosen isoelectric point. The criteria for maximizing buffer capacity is well known, and one preferred approach is to use appropriate mixtures of weak acid and basic buffers wherein the difference between their respective pK-value is less than 2.

The modes of reacting of the BR with the hydroxy groups of the polymers (gels) follow the basic chemistry of di- and triazines. Their reactivity can be enhanced under basic conditions. The components can be mixed and formed into a polymer solution by the followiong different modes:

(1) The components of polymer and BR are mixed at a pH at which they do not react rapidly and after forming a homogeneous solution and degassing, the solution's pH is made more basic to react the polymer, and the polymer is cast into a mold or on a substrate, where it is allowed to gel by either cross-linking and/or cooling. A gel with bound BR moieties is obtained.

(2) The same procedure as in (1) is followed except that after the pH is adjusted to react the BR, the solution is continued to stir prior to degassing and casting; then casting and adjusting the pH to get cross-linking reactions to gel formation.

(3) The solution's pH may be adjusted at the outset of mixing the components and the remainder of the procedures described in (1) and (2) may be followed.

(4) Since both acid and basic BR must be bound to the gels, they may be bound either together in the same polymer solution or in separate polymer solutions, and then, after reaction, the separate polymer solutions may be mixed. The detailed sequence for each solution and/or for the combined polymer solution may be as described in (1) to (3), above, or a combination thereof.

(5) For thermal reversible gels, it is preferable to carry out the binding reaction at the lowest temperature at which the gel is in solution, though higher temperatures may be used. The temperature at which the gel is cast into the mold may be the same at which the binding reaction occurs or it may be a higher temperature where the gel is less viscous and may be poured and degasseal to form a more uniform gel. The gel may be kept at this elevated temperature for some time, where additional binding of the BR may ooccur if it was not completed at the lower temperature.

It is advantageous to carry out the binding reaction at lower temperatures to minimize the hydrolysis rate of the BR, in comparison to maximizing the binding of BR to the polymer. On the other hand, higher temperature may be optimum for casting and degassing because of the reduced viscosity. Alternatively, the BR may be bound to the gel, washed of excess reagent, and then melted, titrated one with the other, and cast into the buffered gel.

For water-soluble polymers which are not thermally reversible gels, the above heating protocols may be followed, or both the binding of the BR and the casting of the derivatized polymer may be carried out at the same temperature. For water-soluble gels, the binding and cross-linking reactions may occur at temperatures of from −10° to 100° C., but preferably between 4° to 90° C. Thermally reversible gels like agarose may be reacted with the BR at 40° to 90° C. and preferably 40° to 60° C. (in order to prevent competitive reactions (hydrolysis) the temperature should be kept—whenever possible—to the minimum in which the polymer solution is still a solution and not a gel), and then raised to 70° to 95° C., preferably 90° C. for casting.

The pH ranges for binding the reagents are, to a certain extent, a function of the polymer stability, and where the BR is required to only bind to the polymer or also to cross-link it. For agarose and other thermally reversible gels the primary task is to bind the buffer moiety. In addition, gels made from naturally occuring polysaccharides, such as agarose, must be reacted under relatively mild pH conditions.

Thus for agarose the dichlorotriazine buffers are reacted at pH values of from about 6.0 to 8.0. Water-soluble and pH stable polymers, such as polyvinyl alcohol, are reacted, in the pH range of 6.0 to 11.0. The more basic the pH range (e.g. 8.0 to 11.0) that can be used for reacting, the less reactive moieties on the BR are necessary to achieve cross-linking; as for example the third chloro atom of the chloro triazine molecule after two chloro atoms have reacted with the buffer group and one hydroxy group of the polymer (gel), repectively.

When starting from monomers a (co)polymerization step is involved in the sequence of reaction steps that lead to the inventive immobilized buffered gels. These methods of preparation comprise e.g.

(1) reacting separately the acid diazine or triazine derivative and the basic diazine or triazine derivative each with a hydroxy group containing neutral polymerizable monomer, (2) titrating the polymerizable compounds of (1) batchwise against each other, (3) casting the mixture of the polymerizable compounds of (2) into a mold, (4) polymerizing the mixture of (3) in the presence of a cross-linker, and optionally together with a comonomer, and (5) gelling the polymeric reaction products of (4); or (1) reacting separately the acid diazine or triazine derivative and the basic diazine or triazine derivative each with a hydroxy group containing neutral polymerizable monomer, (2) separately polymerizing the reaction products of (1), optionally together with a comonomer, (3) titrating the polymeric reaction products of (2) batchwise against each other to form a polymeric mixture of a predetermined single pH-value, or in a continuous manner to form a polymeric mixture of a pH-gradient, and (4) casting the polymeric mixtures of (3) into a mold and gelling them in the presence of a cross-linker.

Copolymerization/cross-linking reactions to produce polymer gels, especially poly-(hydroxyalkyl methacrylates), are known from the state of the art. Initiators that can be used in these reactions include both radical and anionic initiators. Azo-bis-isobutyronitrile (AIBN) is widely used, although there are advantages of the use of azo-bis-methylisobutyrate and other similar chemicals. Peroxides, such as benzoyl or cumyl peroxide, or peracids can be used as well.

Solvents may be added during the polymerization to decrease the viscosity of the solution.

Chain transfer is a typical problem in these reactions. For example, during the polymerization of 2-hydroxyethyl methacrylate in the absence of a cross-linking agent, chain transfer to the polymer may be observed, which leads to the formation of cross-linked poly-(2-hydroxyethyl methacrylate)(PHEMA).

Amongst other properties, the copolymerization of hydrophilic and hydrophobic monomers also allows the control of hydrophilicity. The relatively high hydrophobicity of the usual chemical polymerizable cross-linking agents also affects the overall hydrophilicity of the hydrogel formed, which may, of course, be raised by exchanging the cross-linking agent for a more hydrophilic compound. It must be remembered that, with hydrogels formed by chemical cross-linking, the copolymers obtained depend on the constraints of the copolymerization system, especially with respect to the possible inhomogeneity of composition of the copolymer formed, particularly if the copolymerization parameters differ from each other.

The chemical character of hydrophilic groups differs not only in affinity to water but also, equally important, in polarity. This makes the character of some gels either completely neutral, e.g. PHEMA, or polymers of glucose and sucrose methacrylates—or capable of ionization—e.g. polyacrylic and polymethacrylic acids and coplymers on the basis of (meth)acrylic acid—or basic, such as polyvinyl pyridine and its copolymers and derivatives. negatively and positively charged polymers mixed together can form water-insoluble, but swelling, complexes which behave as hydrogels. For the present invention, however, only neutral polymers which prevent adsorption and electro-osmosis are of interest. One especially neutral gel made by polymerization is that of NAT.

One preferred way to form the immobilized buffered gels and the corresponding membranes by polymerization would be as follows: (Aqueous) solutions of the derivatized (acid/basic) polymerizable monomers are batchwise titrated against each other to achieve the required pH-value, e.g. for PIEF-membranes, and then cast into a configuration; or when the titration is carried out continuously with two different solutions, the mixture is added to a mold to form a pH-gradient. The gradient in this case may be stabilized with e.g. glycerol. After pouring into the mold the mixtures are polymerized in the presence of polymerization initiators, crosslinking agents (monomers), and optionally comonomers, e.g. by applying heat; thus preserving the shape and the pH-gradient. A gel structure is formed, swollen by the solvent. The pore size may, of course, be controlled by the concentration of the cross-linker (and e.g. its hydrophobicity) and the initiator (consistent with mechanical strength), but just as important may be pore-forming agents. Such agents may be leachable polymers (neutral and non-charged), or cosolvents which precipitate the polymers as they are formed.

In an alternate route the acid/basic di- or triazine derivatives (buffering reagents—BR-) may react with the polymerizable monomer or the (formed) polymer in the process of polymerization. Thus, the BR may be added at any time before or during the polymerization. In addition to BR, other materials may be added to facilitate the reaction between them and the hydroxyl groups of the monomers or polymers (matrix). Examples of such additives are catalysts such as tertiary amines, e.g.trimethyl amine, or aromatic or heterocyclic amines, such as optionally substituted pyridines, e.g. 4-(dimethyl)-amino pyridine, or non-nucleophilic proton acceptors, such as diisoprpyl amine, 2,6-lutidine and 2,4,6-collidine. Particularly powerful catalysts are 4-N,N-dimethylamino pyridine and 4-pyrrolidino pyridine.

The hydroxy group containing polymerizable monomers reacted with BR are a further object of the present invention. As indicated above, they can be (co)polymerized in the presence of suitable initiators, cross-linkers, comonomers and optionally other additives to form, after casting into a configuration and gelling, the immobilized buffered gels and membranes, respectively.

Suitable monomers are those mentioned hereinabove for the preparation of the hydroxy group containing polymers; useful BR are also mentioned.

The general reaction scheme to get these compounds is as follows: Polymerizable Monomer-OH+L-BR=Polymerizable Monomer-O-BR+HL (L=nucleophilic leaving group, such as chloro).

The bound acid or basic group molarity may vary from about 10 to 5000 mmol, preferably from 50 to 2000 mmol, and most preferably from 150 or 200 to 1500 mmol per kg of dry gel.

In the case of wet (aqueous) gels, e.g. 2% gels, the amount of said groups comprises only the corresponding part, e.g. the $50^{th}$ part. In the case of wet agarose gels (e.g.2% gels) the preferred range is from 1 to 100(50) mmol, preferably from 1 to 20 mmol, and most preferably from 3 to 15 mmol per kg of wet gel.

The inventive immobilized buffered gels, when formed e.g. in membranes, pH-gradient gel plates or columns, may be used in electrophoretic processes, most preferably in preparative isoelectric focusing electrophoresis (PIEF) for separating amphoteric substances, such as biological materials.

The principle of isoelectric focusing is based on the fact that certain biological materials (such as proteins, peptides, nucleic acids, and viruses) are amphoteric in nature, i.e. they are positively charged in an acid medium and negatively charged in a basic medium. At a particular pH value, called the isoelectric point (pI), these biological materials will have a zero net charge.

Being charged in a pH gradient, the biomaterials migrate under the influence of an electric field until they reach the ph of their isoelectric point. At the isoelectric point (zero net charge), the biomaterials are not influenced by the electric field. Diffusion of "focused" biomaterials away from their pI will cause them to once again become charged, whereby they will electrophoretically migrate back to their pI. Thus, the biomaterials focus into narrow zones from which they can be selectively separated.

The inventive immobilized buffered gels in membrane form can form gel barriers that can be used e.g. in PIEF devices. The barriers are characterized by a constant pH, close to the pI of the target biomaterial (protein), which keeps this protein entrapper within a cell. At the same time, the charged impurities are driven through the gel membranes by an applied electric field perpendicular to the membrane.

The pH of the gel membrane is chosen to be slightly higher or lower than the pI of the target protein (or both membranes may be at the same pH equal to that of the isoelectric point), so that when it occasionally approaches the membrane surface, it acquires electric charge, which causes the protein to be pulled back from the membrane into the central solution. Thus the solution containing the desired material (protein etc.) can be circulated in the feed compartment of the PIEF device, continually removing the impurities and purifying the desired material, which is focused in said compartment. By such a method, proteins can be separated differing by as little as 0.01 pH units in their pKi values (pK of the isoelectric points).

BRIEF DESCRIPTION OF THE INVENTION

The inventive gel membranes are designed for an electrophoretic apparatus (continuous isoelectric focusing device) generically represented in FIG. 1, and known from EP-A-287 513.

Other devices wherein the inventive gels or membranes can be used are described in EP-A-323 948 and EP-A-369 945.

Figure 2:
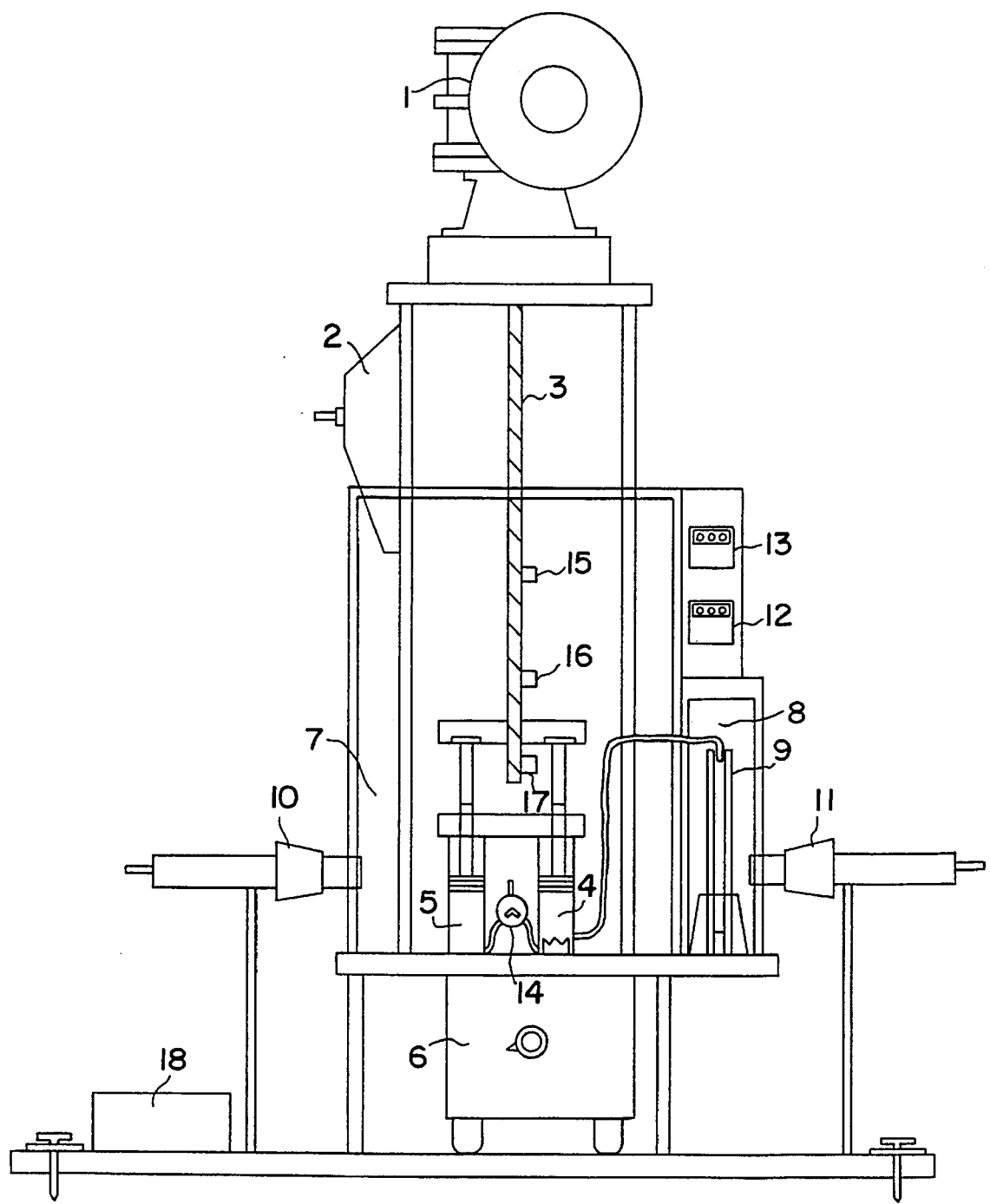

FIG. 2 schematically decribes the general layout of the gradient mixer.

The device of FIG. 1 basically comprises a flow chamber (8), containing the protein feed solution connected with two containers (3) and (4), separated by the gel membrane with immobilized pH barrier (2). The membrane close to the anode (+) may have an isoelectric point just below to the electric point of the protein being purified, and the membrane close to the cathode (−) may have an isoelectric point just above that value.

This device uses an isoelectric focusing technique wherein the protein of interest is not electrophoretically driven into a gel matrix, but is kept in an isoelectric state in the liquid stream, and only the impurities are forced to focus in the gel membrane phases.

Because the electrophoretic separation is performed in a pH gradient, all the species having an isoelectric point within the pH gradient are driven by a voltage gradient to the particular zone where they exhibit zero net charge and in which they remain stationary as long as the electric field is applied. The protein of interest is already isoelectric in the flow chamber (8) which constitutes the sample feed system. Therefore, said protein is not forced to flow by the electric field.

The gel membranes may be regarded as very short pH gradients, covering only a very narrow pH interval. Ideally, the pH interval comprises zero pH units. Furthermore, the pH values of the membranes may have a pH value, which is identical to isoelectric point of the compound of interest. Consequently, identical membranes can be prepared instead of membranes differing from each other.

The currently used membranes are prepared from poyacrylamide gels, which are operating satisfactorily except for their potentially carcinogenic leachables of acrylamide, poor mechanical strength and their sieving effect for very large molecules (above 500 kDa). This toxicity limits their use for human or animal consumptions, as in pharmaceutical applications.

These disadvantages can be overcome by the present invention, and it is one main advantage of the the inventive gels and membranes that they are non-toxic. Other advantages of the inventive gels and membranes are their fixed and constant pH and their good buffer capacity, as well as their conductivity; they show non-sieving behaviour and allow transport of impurity macro-molecules, such as proteins and ionic polysaccharides; electro-osmotic effects can be prevented due to the minimum content of residual ionic groups; further, the gels and membranes eliminate hydrophobic or electrostatic adsorption of macro-molecules because they are hydrophilic and non-charged; and finally, the gels and membranes show particular mechanical and chemical stability.

The commonly used practice for the preparation of immobilized pH-gradient gels (IPG) is to mix a heavy acid solution with a light basic solution in a predetermined and controlled manner, dispense the liquid mixture into a a specially shaped mold (cassette) an solidify the mixture into a gel shaped to a sheet which is approximately 0.5 mm thick, 10 cm long and 10 to 20 cm wide.

The density of the solutions is controlled by appropriate addition of glycerol in such a way as to generate inside the cassette a density gradient.

The density gradient helps to maintain the shape of the pH-gradient during the stages of the gel formation. While, as exemplified, glycerol is used to form the density gradient, the density gradient may well be formed with other substances.

The pH of the solutions is adjusted such that the acidic solution has a pH equal to the basic extreme of the IPG gel.

The available pH gradient mixers are only suitable for the preparation of polyacrylamide gels in which both the acidic and basic solutions have a low viscosity and the mixing is done at ambient temperature.

These mixtures are not suitable for preparing agarose based IPG gels since the agarose solutions are much more viscous and have to be mixed and dispensed into the cassette at the temperature of molten agarose (60° to 80° C.).

Furthermore, to achieve equilibrium for the density gradient in the cassette prior to solidification, the mixed pH gradient has to be kept at elevated temperatures (about 60° C.) for some time.

Thus, the gradient mixer (FIG. 2) for the preparation of agarose based IPG gels—and this is a further object of the present invention—comprises:

a positive displacement syringe dispensing device (4,5) driven by a controlled speed motor (1)

a mixer driven by a magnetically couple stirrer (6)

a temperature controlled circulating air oven for the mixer/dispensing syringes (7)

a cassette into which the mixed solutions of the gels are dipensed and the IPG gel is shaped (9)

a second temperature controlled circulating air oven for the cassette (8).

The mixer is comprised of two 15 ml glass syringes, a basic gel glass syringe (4) and an acidic gel glass syringe (5), which are placed in a closed circulating air oven compartment (7) preheated to the gel melt temperature, usually 70° to 80° C., by an air jet gun (10) (30 l/min, 20° to 80° C.) controlled by a temperature controller and indicator(12).

The melted gel is sucked into the syringes through a three way valve (14) so that the more basic agarose gel is placed in syringe (4) and the more acidic gel is placed in syringe (5), in the procedure where the acidic syringe (5) will contain the glycerol and will have the higher density. If the gel is made with the basic (gel)solution being the heavier solution it will be put in syringe (5) and the acidic (gel)solution in syringe (4).

The design is such as to make sure that no air bubbles are entrapped in the syringes or the connecting tubing.

After filling up the syringes with the respective gels, the variable speed motor (1) (0 to 20 rpm) is started and the excess of gel is pushed out so that a predetermined volume of gel is left in each syringe. That volume is determined accurately and repeatable by the location of the start point switch (16).

In parallel, the cassette (9) (glass plate cassette, e.g. 20×10 cm) is placed in the second circulating air oven (8) which is heated to about 60° C. by the second air gun (11) (30 l/min, 20° to 80° C.) and kept at that temperature for equilibration.

The temperature of the oven (8) is kept constant by the aid of a temperature controller and indicator(13).

When the whole system reaches equilibrium, the magnetic stirrer (6) is started, the three way valve (14) is rotated to a position which connects the two syringes (4)(5), the output flexible tube is placed in the cassette (9) and the motor (1) is started at a speed of about 10 rpm as determined by the motor speed control (2).

As the motor rotates, a load screw (3) pushes down the syringe plungers and melted gel is dispensed from the basic syringe (4) to the cassette. At the same time acidic gel is dispensed from the acidic syringe (5) to the basic syringe (4) gradually increasing the acidity in this syringe. If syringe (5) is the basic one (contains the basic gel solution) and syringe (4) is the acidic one, then the situation is reversed.

Thus the gel which is dispensed to the cassette (9) will have a progressively decreasing pH.

Since the more basic gel is also heavier (the basic syringe contains a mix of agarose gel and 30% of glycerol), the gel dispensed into the cassette also has a gradually decreasing density. This is the particular case for making an IPG with the pH range of 5 to 6 using aem- and gly-derivatives of agarose.

The density gradient imposed on the pH gradient helps to maintain the linear shape of the pH gradient during the dispensing and solidification stages.

There is an upper limit switch (15) and a low limit (stop point) switch (17). When the syringe plungers reach the low limit (stop point) switch (17) the motor is stopped. At that point the cassette (9) has been fully filled with gel.

After the gel in the cassette reaches equilibrium, the oven is shut off, cooled to ambient temperature, and the gel is released from the cassette. The gradient mixer is monitored by an electrical switcing board (18).

The present invention is illustrated by the following examples which should not be considered limiting as to the inventive scope.

Parts and percentages are by weight, if not otherwise indicated. Temperatures are given in degrees Centigrade.

EXAMPLE 1

The method for preparing immobilized buffered agarose (gel) membranes first requires the synthesis of the buffered reagents (BR), their binding to the agarose polymer in separate samples for the acid and basic BR, respectively, and mixing and casting of the sol or solution of the polymeric reaction products.

Preparation of acid and basic derivatives: A solution of 2 ml acetone and 10 ml of ice water containing 0.89 g of cyanuric chloride is added each to (I) and (II).

| (I) Acid derivative: | |
| --- | --- |
| 4-aminobutyric acid (pK = 4.6) | 0.48 g |
| trimethylamine | 2.2 ml |
| sodium hydroxide, 8.6 mmol | 8 ml |
| (II) Basic derivative: | |
| 4-(2-aminoethyl)morpholine (pK = 6.0) | 0.563 g |
| trimethylamine | 2.2 ml |
| sodium hydroxide, 4.2 mmol | 8 ml |

Final concentration of derivatives in each solution is 0.195 M. Preparation of agarose membranes with immobilized pH determining groups: 40 ml of 2% agarose solutions are prepared for casting two PIEF membranes.
(A) 0.4 g of agarose (Type VIII-Sigma A-4905) are dissolved in 16 ml of deionized water and heated to 90° C. for half an hour. This solution will be derivatized with the aminobutyric acid buffer (I).
(B) An agarose solution as in (A) is prepared for reaction with the morpholine buffer (II).
(C) Both solutions are heated and kept at 50° C. for 40 minutes.
(D) 4 ml of an ice cold aqueous solution of dichlorotriazine aminobutyric acid (pK=4.6) are added slowly (3–4 minutes) to one of the solutions of (C).
(D) 4 ml of an ice cold aqueous solution of dichlorotriazine aminoethyl morpholine (pK=6.2) are added slowly (3–4 minutes) to the other solution of (C).
(F) Calculated amounts of solutions (D) and (E) are mixed at 90° C. for one hour to get the desired pH.
(G) The solution of (F) is poured into the PIEF mold (90 cm in diameter and 3 mm deep) at 90° C., covered with a glass plate and left to gel.

The obtained gel membranes are designed to clean the protein Eglin with a pI of 5.50. Therefore, the membrane on the anodic side was made with a BR concentration to give a buffered pH of 5.45, while the cathodic membrane was buffered to 5.80. These membranes are then placed in the PIEF device according to FIG. 1. The details of each duplicate run (batches 1 and 2) are given in Tables 1 and 2. Impurities of the Elgin samples are separated within 0.05 pH units. 91% of protein recovery is achieved. Cleaning of impurities improves as a function of time. Cleaning for a longer period of time would get rid of the remaining impurities.

EXAMPLE 2

The procedure of Example 1 is repeated, but the acid and the basic buffered agarose products are prepared individually by heating them in solution, cooling the sol to form a gel, and then the gel is cleaned of unreacted monomers and reagents (e.g. by dialysis and/or electrophoresis), and the basic agarose products is then titsated in the melt form with the acid agarose product to give the desired pH of 5.5. The results in cleaning Eglin are even better than in Example 1.

EXAMPLE 3

In another variation of preparing the acid/basic triazine derivatives on the agarose matrix, the 2% agarose gel is washed with acetone to replace water; the agarose gel is then reacted with cyanuric chloride in acetone at 0° C. for 30 minutes, and washed with acetone to take out the unreacted cyanuric chloride. The agarose dichloro triazine derivative is then immersed in an acetone solution of the amino butyric acid or aminoethyl morpholine for 10 hours, the gel is then removed from the solution and washed. PIEF membranes are made by dissolving the derivatives at 50° C. in water, titrating the basic derivative with the acid one to get gels of pH 5.8 and 5.65, and casting them into membranes. These membranes cleaned Eglin on both sides of the anodic and cathodic bonds.

EXAMPLE 4

In another variation of making agarose derivatives, the dichloro triazine amino butyric acid and aminoethyl morpholine each are dissolved in acetone or an acetone-water solution at 0° to 4° C., proton acceptors are added, such as diisopropylethyl amine or N,N-dimethylaniline, and reacted with agarose gel swollen with acetone for 10 to 72 hours, drained, washed and then used as in Example 3.

EXAMPLE 5

The agarose derivatives of Example 4 are titsated one against the other with a pH gradient mixer according to FIG. 2. In this case, however, dichloro triazinyl glycine was used instead of the aminobutyric acid derivative. The resultant gel (in a cassette) has a linear immobilized gradient from pH 5 to pH 6 over a 10 cm length.

The single steps can be defined as follows:

prepare agarose-cycl-gly and agarose-cycl-aem derivatives;

Melt the gels and prepare solutions of:

agarose-cyclogly (light))

agarose-cycl-aem+glycerol (heavy);

Create a pH gradient by the gradient former of FIG. 2. Solidify the gradient pH gel at 25° to 30° C. (cycl=cyanuric chloride; gly=glycine; aem=aminoethyl morpholine).

EXAMPLE 6

A. Preparation of 100 ml of a 2% agarose gel with 5 to 6 meq/kg (milliequivalents per kilogram) of 2% swollen gel bound aminoethyl morpholine (aem).

(1) Preparation of dichlorotriazinyl-aminoethyl morpholine:

(a) 1.6 g (8.7 mmol) of fresh crystallized cyanuric chloride are dissolved in 24 ml of acetone cooled to 0° C.

(b) To 0.35 g (8.7 mmol) of sodium hydroxide dissolved in 16 ml of water, cooled to 0° C., 1.36 ml (10.4 mmol) of 4-(2-aminoethyl)-morpholine (aem) are added.

Solution (b) is then slowly added to solution (a) while stirring and cooling to 0° to 4° C. Stirring is continued at this temperature for 30 minutes.

(2) Preparation of the agarose-cyanuric chloride-aem product:

2 g of agarose (Sigma A-4905) are placed into a 250 ml three-necked flask. After adding 60 ml of aleionized water, the mixture is stirred at room temperature for 10 minutes. The temperature is then raised to 90° C. under stirring until dissolution of the agarose. The temperature is then decreased to 50° to 55° C. and the gel is equilibrated at this temperature. The pH is adjusted to a value of 9 to 10 with 0.1N sodium hydroxide solution. 20 ml of solution (1) is added, and the pH is adjusted to 9 to 10 with 0.1N sodium hydroxide solution. The mixture is stirred at 50° C. for 1 hour, maintaining the pH at 9 to 10. Then an additional 20 ml of solution (1) is added, keeping the pH at 9 to 10. Stirring is continued for an additional one hour at 50° C., then 1.1 ml (8.5 mmol) of aem in a mixture of 6 ml of acetone and 2 ml of water is added.

The temperature is then raised to 85° to 90° C. and the reaction mixture is stirred at this temperature for one hour. The solution is then poured into a glass mold which is 20 cm long, 10 cm wide and 5 mm deep. The mold is left at room temperature for 3 hours and then stored at 4° C. for 12 hours.

The mold is then cut into pieces (1×1) and then washed as follows: 2 times with 1 l of an acetone/water mixture (80/20), 2 times with 1 l of deionized water, 2 times with 1 l of water acidified to pH 4, 2 times with 1 l of deionized water, 3 times with 1 l of water of pH 1 l (1 hour each), and then with aleionized water until the pH of water is achieved.

B. Preparation of of 100 ml of a 2% agarose gel with 6 to 7 meq/kg bound glycine.

(3) Preparation of dichlorotriazinyl-glycine:

(a) 1.6 g (8.7 mmol) of cyanuric chloride are dissolved in 20 ml of acetone and 4 ml of cold deionized water; the solution is then cooled to 0° C.

(b) 0.78 g (10.4 mmol) of glycine and 0.42 g (10.4 mmol) of sodium hydroxide are dissolved in 10 ml of cold deionized water; the solution is then cooled to 0° to 4° C.

(c) 0.34 g (8.7 mmol) of sodium hydroxide are disolved in 6 ml of aleionized water. Solution (b) is then slowly added to solution (a) at 0° C.; the pH is adjusted to 6.7 by adding solution (c). The obtained reaction solution is stirred for 20 minutes at 0° to 4° C.

(4) Preparation of the agarose-cyanuric chloride-glycine product:

Procedure (2) is repeated, by using solution (3) instead of solution (1) and adding 0.64 g of glycine in 4 ml of aleionized water in the last step.

The following washing procedure is used: 2 times with 1 l of deionized water, 2 times with 1 l of water of pH 4, 2 times with 1 l of deionized water, 2 times of 1 l of water of pH 8, 2 times of 1 l of deionized water, 3 times with 1 l of pH 3 (1 hour each), and finally with deionized water until the pH of the water is achieved (3 to 4 l).

A pH gradient gel of between pH 5 to 6 is made from the above derivatives using the gradient gel mixer in the following way: (1) The aem/agarose derivative is titrated to a pH of 4.9 with the glycine/agarose derivative to give the "acidic solution", and to pH 6.1 to give the "basic solution".

(2) Using the gradient maker, the basic solution is titrated continuously with the acidic solution to give the required pH gradient.

Mixtures of protein markers (pI 5.1, 5.4, and 5.9) are separated on this IPG gel. The results show a good separation and an almost linear pH gradient. In addition the individual markers are resolved into their components showing a resolution of 0.02 pH units. These same mixtures of protein markers are resolved into patterns with the same band positions showing the uniformity along the length of the gel. The same approach can be used to make gels in a range of e.g. pH 2 to 10 using the appropriate buffer derivatives, as shown in the following Example 7.

EXAMPLE 7

The necessary dichlorotriazines for each pH range are synthesized and used to prepare the agarose derivatives for the buffers and titrants. The reaction of the agarose with the the dichlorotriazines is conducted in aqueous solutions at the required concentrations (for details cf. Example 6 and the other foregoing examples) to give an acidic or basic capacity between 4 to 20 meq/kg of a 2% wet gel. The agarose derivatives are then used as either buffers or titrants, depending on the IPG gel being made.

The following reactive dichlorotriazine derivatives are used:

|  | pK[1] | Agarose gel capacity (meq/kg of 2% wet gel) |
|---|---|---|
| Basic derivatives | | |
| R—NH—$(CH_2)_2$—$N(CH_2)_4O$ [2] | 6.2 | 6.7 |
| R—NH—$(CH_2)_3$—$N(CH_2)_4O$ [3] | 7.0 | 4.3 |
| R—NH—$(CH_2)_2$—N—$H(CH_3)_2$ [4] | 8.5 | 7.5 |
| R—NH—$(CH_2)_3$—N—$H(CH_3)_2$ [5] | 9.3 | 14 |
| Acidic derivatives | | |
| R—NH—$CH_2COOH$ [6] | 3.6 | 9.3 |
| R—NH—$(CH_2)_3$—COOH [7] | 4.6 | 12.9 |

[1] These values are taken from polyacrylamide-immombilines; for the triazinyl derivatives bound to agarose the pK's may be different.
[2] 4-(2-Aminoethyl)-morpholine derivative (AEM)
[3] 4-(2-Aminopropyl)-morpholine derivative (APM)
[4] N,N-Dimethylethylenediamine derivative (DMEDA)
[5] N,N-Dimethylpropylenediamine derivative (DMPDA)
[6] Glycine derivative (GLY)
[7] 4-Aminobutyric acid derivative (ABA)

The agarose derivatives are mixed at a temperature at which they are melted (usually about 60° C.), while the IPG solid gel is used in analytical IEF (isoelectric focusing) at 10° C. Since the pH of the gel is temperature-dependent, this dependency has to be considered in order to predict the gel's pH at 10° C., based on the known titrated pH at 60° C. Thus, the operational steps are:

The agarose buffer is titrated with the agarose to the basic extreme of the gel.

The pH vs. temperature dependency is determined and the pH at 10° C. is calculated.

The pH at 60° C. is readjusted to get the desired pH at 10° C.

A similar operational approach is conducted with the acidic pH extreme of the IPG.

To generate a linear pH gradient, a constant buffer capacity over the gradient is required. To achieve this constant buffer capacity, the concentration of the buffering species is adjusted so that the concentration of buffer increases, going to the pH extreme farthest from the pK of the buffer. In this case it is achieved by the addition of glycerol to the appropriate buffer/titrant solution.

pH-range: 4 to 5

In this range the ABA-derivative (pK 4.7) is used as the buffer and titrated with the DMPDA-derivative (pK 9.3). The pH vs. temperature curve for the acidic and basic extremes showed the need to titrate a 60° C. solution at pH 4.7 with a solution at pH 5.5 to get an IPG gel of pH 4.0 to 5.0. The first gel, however is titrated to pH 4.4 and 5.0 at 60° C. to give a pH range of 4.0 to 4.7 at 10° C.

The gel shows a good separation of protein markers 4.2 and 4.6.

pH-range: 5 to 6 (cf. Example 6)

pH-range: 6 to 7

In this range the buffer is the APM-derivative and the titrant is the GLY-derivative. The pH vs. temperature curve fixes the acidic side at pH 5.2 and the basic side at pH 6.5 at 60° C. for achieving a functioning gel in the range of pH 6 to 7 at 10° C.

pH-range: 7 to 8

An IPG gel in this range is made with the DMEDA-derivative as the buffer and the GLY-derivative as the titrant. A good separation between the markers 7.4 and 7.2 is achieved, although the pK of the buffer (8.5') is outside of the IPG range of 7 to 8.

TABLE 1

|  |  |  |  |  |  | % Protein Recovery = 91% batch 1 |
|---|---|---|---|---|---|---|
| Time (min) | 1 | 7 | 29 | 32 | 72 | 83 |
| Volt | 300 | 825 | 1072 | 1067 | 1056 | 1059 |
| mA | 30 | 30 | 28 | 28 | 28 | 28 |
| Watt | 9 | 25 | 30 | 30 | 30 | 30 |
| pH | 7.3 | 5.8 | 5.2 | 5.3 | 5.5 | 5.5 |
| μS | 9.5 | 1.8 | 1.4 | 1.4 | 1.4 | 1.4 |

EXPERIMENTAL CONDITIONS

| Cathodic Reservoir | Membranes | Center channel | Membrane 2 | Anoid reservoir |
|---|---|---|---|---|
| 1 mM NaOH 125 ml | pH: appx. 5.8 | 2 mg/ml EGLIN 100 ml | pH: appx. 5.45 | 1 mM Acetic Acid 125 ml |

TABLE 2

|  |  |  |  |  |  | % Protein Recovery = 91% batch 2 |
|---|---|---|---|---|---|---|
| Time (min) | 1 | 6 | 7 | 30 | 68 | 80 |
| Volt | 303 | 565 | 1000 | 1052 | 1027 | 1030 |
| mA | 30 | 30 | 29 | 29 | 29 | 29 |
| Watt | 9 | 17 | 30 | 30 | 30 | 30 |
| pH | 7.4 | 6.2 | 5.8 | 5.5 | 5.5 | 5.5 |
| μS | 12 | 2.5 | 1.5 | 1.4 | 1.4 | 1.4 |

EXPERIMENTAL CONDITIONS

| Cathodic Reservoir | Membranes | Center channel | Membrane 2 | Anodic reservoir |
|---|---|---|---|---|
| 1 mM NaOH 125 ml | pH: appx. 5.8 | 2 mg/ml EGLIN 80 ml | pH: appx. 5.5 | 1 mM Acetic Acid 125 ml |

We claim:

1. A gradient mixer for the preparation of immobilized pH-gradient gels which comprises (A) a first temperature-controlled circulating air oven (7) comprising
- (a) a glass syringe (4) fitted with a plunger and an output flexible tube, and being adapted to receive a basic or an acidic gel;
- (b) a glass syringe (5) fitted with a plunger and adapted to receive a basic or an acidic gel, provided that if syringe (4) contains a basic gel, then syringe (5) contains an acidic gel, and vice versa;
- (c) a magnetic mixer (6) adapted to mix said basic and acidic gels;
- (d) a load screw (3) driven by a motor (1) at a speed determined by a motor speed controller (2) having an upper limit switch (15) and a stop point (low limit) switch (17), load screw (3) being adapted to depress the respective plungers of the syringes (4) and (5) and eject said basic and acidic gels from the respective syringes (4) and (5);
- (e) a rotatable three way valve (14) connecting syringes (4) and (5);
- (f) an air jet gun (10) adapted to heat said oven (7); and
- (g) a temperature controller and indicator (12) adapted to control the temperature of said oven (7);

(B) a second temperature-controlled circulating air oven (8) comprising
- (a) a cassette (9) adapted to receive molten gel directly from syringe (4) via said output flexible tube, and to receive a mixed solution of said basic and acidic gels via said syringe (5), said valve (14), syringe (4) and said output flexible tube, the volume of said mixed solution being controlled by said upper limit switch (15) and said stop point (low limit) switch (17);
- (b) an air jet gun (11) adapted to heat said oven (8); and
- (c) a temperature controller and indicator (13) adapted to control the temperature of said oven (8); and (C) an electric switching board (18) adapted to monitor said gradient mixer.

* * * * *